United States Patent
Wiktor

(10) Patent No.: US 10,335,529 B2
(45) Date of Patent: Jul. 2, 2019

(54) EXTRA-CORPOREAL BLOOD TREATMENT DEVICE AND METHOD FOR SWITCHING OFF OR REDUCING THE SPEED OF A NON-OCCLUDING PUMP IN A FLUID SYSTEM OF AN EXTRA-CORPOREAL BLOOD DEVICE

(71) Applicant: FRESENIUS MEDICAL CARE DEUTSCHLAND GMBH, Bad Homburg (DE)

(72) Inventor: Christoph Wiktor, Gelnhausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 341 days.

(21) Appl. No.: 14/907,460

(22) PCT Filed: Jul. 18, 2014

(86) PCT No.: PCT/EP2014/065558
§ 371 (c)(1),
(2) Date: Jan. 25, 2016

(87) PCT Pub. No.: WO2015/011063
PCT Pub. Date: Jan. 29, 2015

(65) Prior Publication Data
US 2016/0175507 A1    Jun. 23, 2016

(30) Foreign Application Priority Data
Jul. 25, 2013    (DE) .................. 10 2013 012 366

(51) Int. Cl.
*A61M 1/16*    (2006.01)
*A61M 1/36*    (2006.01)
(Continued)

(52) U.S. Cl.
CPC ........ *A61M 1/1601* (2014.02); *A61M 1/1018* (2014.02); *A61M 1/1621* (2014.02);
(Continued)

(58) Field of Classification Search
None
See application file for complete search history.

(56) References Cited

U.S. PATENT DOCUMENTS 3,946,731 A * 3/1976 Lichtenstein ........... A61M 1/16
128/DIG. 3
7,087,033 B2    8/2006 Brugger et al.
(Continued)

FOREIGN PATENT DOCUMENTS

DE        27 03 163 A1    7/1977
DE    10 2010 035498 A1    3/2012
(Continued)

OTHER PUBLICATIONS

International Preliminary Report on Patentability in PCT/EP2014/065558, dated Feb. 4, 2016.
(Continued)

*Primary Examiner* — Richard C Gurtowski
(74) *Attorney, Agent, or Firm* — Kilyk & Bowersox, P.L.L.C.

(57) ABSTRACT

An extracorporeal blood treatment apparatus having a fluid system and a pump for conveying fluid in the fluid system, wherein the pump is a non-occluding pump, and a method for shutting off or reducing the speed of rotation of a non-occluding pump in a fluid system of an extracorporeal blood treatment apparatus. The apparatus and the method are characterized in that before the speed of rotation is reduced or the pump is shut off, the fluid flow into the feed line and out of the discharge line is first interrupted, and after a predetermined time interval after interruption of the fluid
(Continued)

flow has elapsed, the speed of rotation of the pump is reduced or the pump is shut off. The time-delayed shut-off of the pump prevents a reverse flow of fluid, particularly of blood into the arterial blood line, even in the absence of occlusion. As a result of the time-delayed shut-off or reduction in the speed of rotation of the pump, however, an excess pressure is produced in the fluid system. Therefore the blood treatment apparatus and the method provide for countermeasures to prevent uncontrolled fluid flow when the shut-off elements are opened, due to the excess pressure.

22 Claims, 3 Drawing Sheets

(51) Int. Cl.

| | | |
|---|---|---|
| *A61M 1/10* | (2006.01) | |
| *B01D 61/14* | (2006.01) | |
| *B01D 61/24* | (2006.01) | |
| *B01D 61/28* | (2006.01) | |
| *B01D 61/30* | (2006.01) | |
| *B01D 61/32* | (2006.01) | |

(52) U.S. Cl.
CPC ......... *A61M 1/3621* (2013.01); *B01D 61/145* (2013.01); *B01D 61/243* (2013.01); *B01D 61/28* (2013.01); *B01D 61/30* (2013.01); *B01D 61/32* (2013.01); *A61M 1/101* (2013.01); *A61M 1/1006* (2014.02); *A61M 1/1086* (2013.01); *A61M 2205/3334* (2013.01)

(56) References Cited

U.S. PATENT DOCUMENTS

| | | | | |
|---|---|---|---|---|
| 2004/0243046 A1* | 12/2004 | Brugger | ............... | A61M 1/3626 604/4.01 |
| 2007/0060786 A1* | 3/2007 | Gura | ................... | A61M 1/1696 600/16 |
| 2013/0240443 A1* | 9/2013 | Gronau | ................... | A61M 1/16 210/646 |

FOREIGN PATENT DOCUMENTS

| | | |
|---|---|---|
| DE | 10 2012 004 970 A1 | 9/2013 |
| EP | 0 378 251 A2 | 7/1990 |
| EP | 1 086 712 A2 | 3/2001 |
| EP | 1 909 864 A2 | 4/2008 |
| GB | 1 556 293 A | 11/1979 |
| WO | 2006-135934 A2 | 12/2006 |

OTHER PUBLICATIONS

International Search Report from PCT/EP2014/065558, dated Oct. 29, 2014.

* cited by examiner

EXTRA-CORPOREAL BLOOD TREATMENT DEVICE AND METHOD FOR SWITCHING OFF OR REDUCING THE SPEED OF A NON-OCCLUDING PUMP IN A FLUID SYSTEM OF AN EXTRA-CORPOREAL BLOOD DEVICE

CROSS REFERENCE TO RELATED APPLICATIONS

The present application is the national stage entry of International Patent Application No. PCT/EP2014/065558, filed on Jul. 18, 2014, the disclosure of which is expressly incorporated herein by reference in its entirety, and claims priority to Application No. DE 10 2013 012 366.6, filed in the Federal Republic of Germany on Jul. 25, 2013.

FIELD OF INVENTION

The invention relates to an extracorporeal blood treatment apparatus having a fluid system and a pump for conveying fluid in the fluid system, wherein the pump is a non-occluding pump. Furthermore, the invention relates to a method for shutting off or reducing the speed of rotation of a non-occluding pump in a fluid system of an extracorporeal blood treatment apparatus.

BACKGROUND

Various methods are known for extracorporeal blood treatment, for example hemodialysis, hemofiltration, as well as a combination of these two methods, which is called hemodiafiltration. The extracorporeal blood treatment apparatuses have a blood treatment unit that is divided, by means of a semi-permeable membrane, into a blood chamber and a dialysis fluid chamber. During blood treatment, the blood of the patient flows in an extracorporeal blood circuit, through the blood chamber of the dialyzer, while dialysis fluid flows through the dialysis fluid chamber of the dialyzer in a dialysis fluid system. The extracorporeal blood circuit and the dialysis fluid system are referred to hereinafter, in general, as the fluid system of the extracorporeal blood treatment apparatus.

Peristaltic pumps are generally used for conveying the fluids in the fluid system in the extracorporeal blood treatment apparatuses, in which pumps at least one occlusion body moves along the elastic tubular line that serves as the pump chamber. These pumps are therefore also often referred to as occluding tube pumps. The most common occluding tube pump is a roller pump into which a section of the tubular line is laid.

However, extracorporeal blood treatment apparatuses are also known in which, instead of peristaltic pumps, non-occluding pumps, for example centrifugal pumps or impeller pumps are used, which do not have an occlusion body with which the tubular line is occluded.

Shutting off occluding pumps or reducing the speed of rotation of these pumps in the fluid system of the extracorporeal blood treatment apparatus proves to be non-problematic, in practice, because due to the occlusion body, there is no risk of reverse flow of the fluids. In the case of non-occluding pumps, in contrast, there is a risk that fluid, particularly blood of the patient, will flow counter to the conveying direction when the pump is shut off or its speed of rotation is reduced.

SUMMARY

The invention is based on the task of creating an extra-corporeal blood treatment apparatus in which uncontrolled flow of fluids in the fluid system is avoided.

Furthermore, it is a task of the invention to indicate a method for shutting off or reducing the speed of rotation of a non-occluding pump, with which uncontrolled fluid flow in a fluid system of an extracorporeal blood treatment apparatus can be avoided.

The fluid system of the extracorporeal blood treatment apparatus, in which the non-occluding pump for conveying fluid is provided, can be the extracorporeal blood circuit or the dialysis fluid system of the blood treatment apparatus. In the extracorporeal blood circuit, reverse flow of the blood of the patient when the non-occluding blood pump is stopped or its speed of rotation is reduced is supposed to be avoided. In the dialysis fluid system, it can be advantageous to avoid uncontrolled reverse flow of dialysis fluid when the dialysis fluid pump is shut off or its speed of rotation is reduced, particularly when using flow sensors for equalization.

The apparatus according to the invention and the method according to the invention are characterized in that before the speed of rotation of the pump is reduced or the pump is shut off, the fluid flow into the feed line and out of the discharge line is first interrupted, and after a predetermined interval has elapsed after interruption of the fluid flow, the speed of rotation of the pump is reduced or the pump is shut off. The time-delayed shut-off of the pump prevents reverse flow of fluid, particularly blood into the arterial blood line, even in the absence of occlusion of the pump. As a result of the time-delayed shut-off or reduction in the speed of rotation of the pump, however, an excess pressure is produced in the fluid system. Therefore the blood treatment apparatus according to the invention and the method according to the invention provide for counter-measures for preventing uncontrolled fluid flow when the shut-off elements are opened, as the result of the excess pressure.

The blood treatment apparatus according to the invention has a first shut-off element for shutting off the feed line and a second shut-off element for shutting off the discharge line, as well as a control unit for controlling the first and the second shut-off element, as well as the non-occluding pump. The control unit is configured in such a manner that before reduction of the speed of rotation or shut-off of the pump, the first and the second shut-off element are closed, and after a predetermined time interval has elapsed after the first and the second shut-off element were closed, the speed of rotation of the pump is reduced or the pump is shut off.

The predetermined time interval after which, when it has elapsed, the speed of rotation of the pump is reduced or the pump is shut off, can be a fixed, predetermined time interval, which is stored in a memory of the control unit, for example. As an example, the pump can be stopped with a time delay of 0.5 to 2 seconds, preferably 0.5 to 1.5 seconds, after the two shut-off elements have been stopped.

However, a preferred embodiment of the invention does not provide for reducing the speed of rotation or stopping the pump after a fixed, predetermined time interval, but rather the speed of rotation of the pump is reduced at a point in time, or the pump is shut off at a point in time when the flow of fluid through the line is less than a predetermined limit value. The limit value can be a value greater than or equal to zero. Preferably, the limit value is slight greater than or equal to zero, so that the pump is shut off when the flow through the line is close to the zero point or is zero. In practice, shut-off of the blood pump will be sufficient if the through-flow is approaching the zero point.

If the pump is disposed in the feed line, the through-flow is measured in the feed line. For this purpose, the apparatus according to the invention has a device for measuring the flow through the feed line. Before the first and the second shut-off element are opened, reduction of the excess pressure that has built up in the fluid system is required for a controlled fluid flow. The apparatus according to the invention and the method according to the invention provide for different counter-measures for this purpose.

In a preferred embodiment, the blood treatment apparatus has a device for reducing the excess pressure in the fluid system, wherein the control unit is configured in such a manner that after the speed of rotation is reduced or the pump is shut off, the device for reducing the excess pressure before the first and the second shut-off element are opened is activated, so that the excess pressure in the fluid system is reduced. After the excess pressure is reduced, the shut-off elements can be opened at the same time or one after the other, without any risk of an uncontrolled fluid flow.

A preferred embodiment of the devices provides for reduction of the excess pressure by means of a ventilation valve that is activated by the control unit. The ventilation valve is preferably provided on an air separator, particularly a drip chamber, which is generally disposed in the blood discharge line of the extracorporeal blood circuit.

In an alternative embodiment, pressure reduction takes place by way of the semi-permeable membrane of the dialyzer. Because the known blood treatment apparatuses generally have an ultrafiltration device, the pressure reduction can advantageously take place in that the control unit controls the ultrafiltration device in such a manner that fluid (ultrafiltrate) is extracted from the fluid system before the shut-off elements are opened.

A further preferred embodiment provides, in order to avoid an uncontrolled reverse flow, that first the second shut-off element in the discharge line is opened at a first point in time, and only then is the first shut-off element in the feed line opened at a second point in time. In the extracorporeal blood circuit, reverse flow of blood into the arterial blood line is reliably prevented by opening the venous shut-off element before the arterial shut-off element.

An uncontrolled fluid flow is prevented, in a further preferred embodiment, in that a negative pressure is built up in the fluid system before opening the shut-off elements. For this purpose, the non-occluding pump is turned on before the shut-off elements are opened. The pump is preferably operated at a predetermined speed of rotation, so that the predetermined partial vacuum builds up. Monitoring of the partial vacuum can take place using the known pressure sensors that are present in the fluid system of the known blood treatment apparatuses in any case.

The individual method steps for building up the excess pressure in the fluid system can be carried out before canceling out the interruption of the fluid flow, individually or also in any desired combination.

In the following, different exemplary embodiments of the invention will be explained in greater detail, making reference to the drawings.

DETAILED DESCRIPTION

Figure 1:
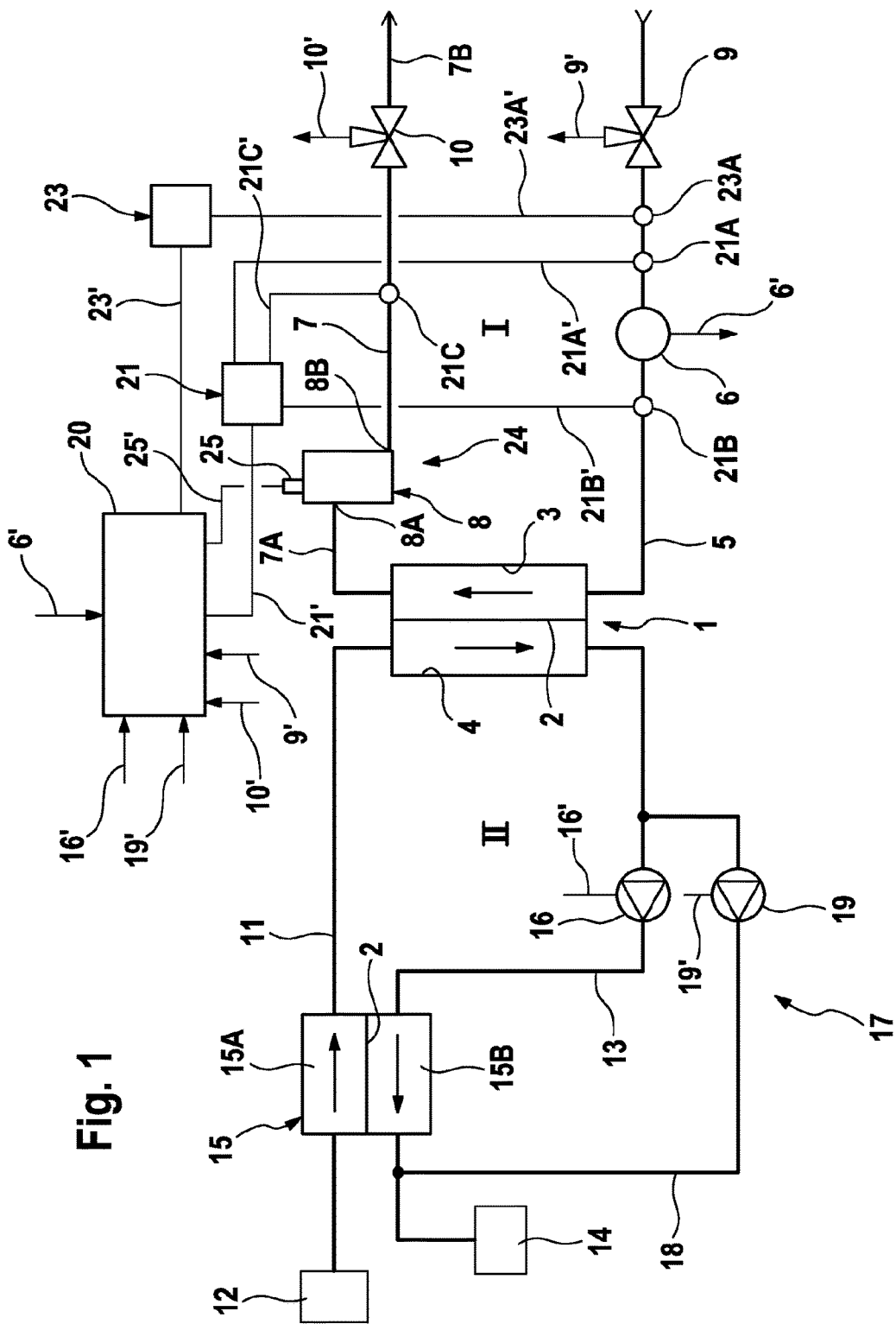
FIG. 1 shows the essential components of an extracorporeal blood treatment apparatus in a simplified schematic representation.

The blood treatment apparatus, particularly a hemo(dia) filtration apparatus, has a dialyzer 1 as a blood treatment unit, which is divided into a blood chamber 3, through which blood flows, and a dialysis fluid chamber 4, through which dialysis fluid flows, by means of a semi-permeable membrane 2. An arterial blood feed line 5 leads to the inlet of the blood chamber 3, in which line a blood pump 6 is positioned, while a venous discharge line 7 leads away from the outlet of the blood chamber 3. The blood discharge line 7 has a first section 7A that leads to the inlet 8A of an air separator 8, particularly a drip chamber, and a second section 7B that leads away from the outlet 8B of the air separator 8. An arterial and a venous cannula, respectively, not shown, are situated on the blood feed line and blood discharge line 5, 7, for connecting to the patient.

Upstream from the blood pump 6, a first shut-off element 9 is positioned in the blood feed line 5, and a second shut-off element 10 is positioned in the blood discharge line, downstream from the air separator 8. The first and the second shut-off element 9, 10 can be tube clamps that can be activated electromagnetically or pneumatically.

The blood feed line and the blood discharge line 5, 7, together with the blood chamber 3, form the extracorporeal blood circuit I of the blood treatment apparatus. In the following, the dialysis fluid system II of the blood treatment apparatus will be described.

The dialysis fluid system II has a dialysis fluid feed line 11 that leads from a dialysis fluid source 12 to the dialysis fluid chamber 4 of the dialyzer 1, and a dialysis fluid discharge line 13 that leads away from the dialysis fluid chamber 4 of the dialyzer 1 and to an outlet 14.

A chamber 15A of an equalization device 15 is positioned in the dialysis fluid feed line 11, while another chamber 15B of the equalization device 15 for balancing out fresh dialysis fluid with used dialysis fluid is positioned in the dialysis fluid discharge line 13. A dialysis fluid pump 16 is situated upstream from the equalization device 15, in the line section 11A of the dialysis fluid discharge line 13.

For extraction of fluid (ultrafiltrate) from the blood by way of the semi-permeable membrane 2 of the dialyzer 1, the blood treatment apparatus has an ultrafiltration device 17. The ultrafiltration device 17 has a fluid line 18 that branches off from the dialysis fluid discharge line 13 upstream from the equalization device 15 and leads directly to the outlet 14, in which line an ultrafiltrate pump 19 is situated.

Furthermore, the blood treatment apparatus has a central control unit 20. The blood pump 6, dialysis fluid pump 16, and the ultrafiltrate pump 19, as well as the first and the second shut-off element 9, 10 are connected with a central control unit 20 by way of control lines 6', 16', 19', 9', 10', so that the control unit 20 can operate the pumps at a predetermined speed of rotation and can open or close the first and the second shut-off element 9, 10.

Furthermore, the blood treatment apparatus has a pressure measurement device 21 for measuring the pressures in the extracorporeal blood circuit I, which device has a first sensor 21A for measuring the arterial pressure $p_{art}$ in the blood feed line 5 upstream from the blood pump 6, a second sensor 21B for measuring the pressure $p_{pre}$ in the blood feed line 5 downstream from the blood pump 6 and upstream from the dialyzer 1, and a third sensor 21C for measuring the venous pressure $p_{ven}$ in the blood discharge line 7 downstream from the air separator 8, which sensors are connected with the pressure measurement device 21 by way of signal lines 21A', 21B', 21'.

The pressure measurement device 21 sends the pressure signals to the central control unit 20 by way of a data line 21'.

To measure the flow $Q_b$ of blood, the blood treatment apparatus has a through-flow measurement device 23 that has a sensor 23A in the blood feed line 5 upstream from the blood pump 6, which sensor is connected with the through-flow measurement device by way of a signal line 23A'. The through-flow measurement device 23 is connected with the central control unit 20 by way of a signal line 23'.

The blood treatment apparatus can also have further components, but for the sake of better comprehension, they are not shown. However, to carry out the method according to the invention, it is not necessary that the blood treatment apparatus has all of the sensors described above.

The central control unit 20 is configured in such a manner that the individual components of the blood treatment apparatus are controlled in such a manner that the steps required to carry out the method according to the invention are performed. For this purpose, the control unit 20 can have a data processing unit (microprocessor) on which a data processing program (software) runs.

The blood pump 6 is a non-occluding blood pump that does not have an occlusion body for closing off the tube line. The non-occluding pump can be a centrifugal pump or an impeller pump, for example.

Figure 2:
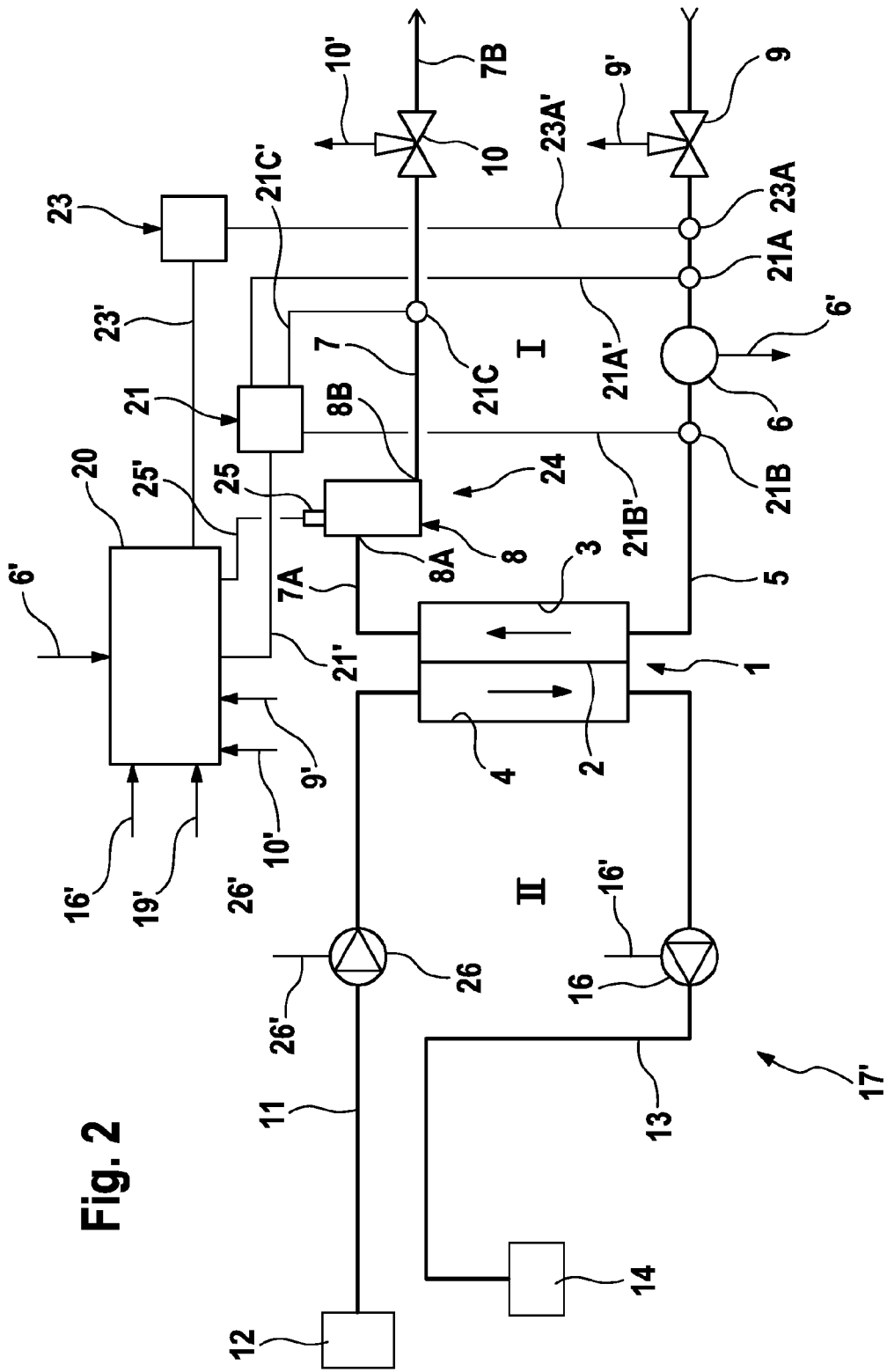
FIG. 2 shows an alternative embodiment of the blood treatment apparatus in a simplified schematic representation.

FIG. 2 shows an alternative embodiment of the blood treatment apparatus, which differs from the exemplary embodiment of FIG. 1 only in that the equalization of fresh and used dialysis fluid takes place by means of adjusting the conveying rates of the dialysis fluid pump 16 disposed in the dialysis fluid discharge line 13 and of a dialysis fluid pump 26 disposed in the dialysis fluid feed line 11, which latter pump is connected with the central control unit 20 by way of a control line 26'. A predetermined amount of dialysis fluid can be extracted from the dialysis fluid system by means of setting different conveying rates of the two pumps 16, 26 (ultrafiltration). In the alternative embodiment, a separate ultrafiltration pump is not provided. Also, no equalization chambers are provided. The ultrafiltration device 17' of the alternative embodiment comprises the dialysis fluid pump 16 disposed in the dialysis fluid discharge line 13 and the dialysis fluid pump 26 disposed in the dialysis fluid feed line 11. The parts that correspond to one another are provided with the same reference symbols in FIGS. 1 and 2.

Figure 3:
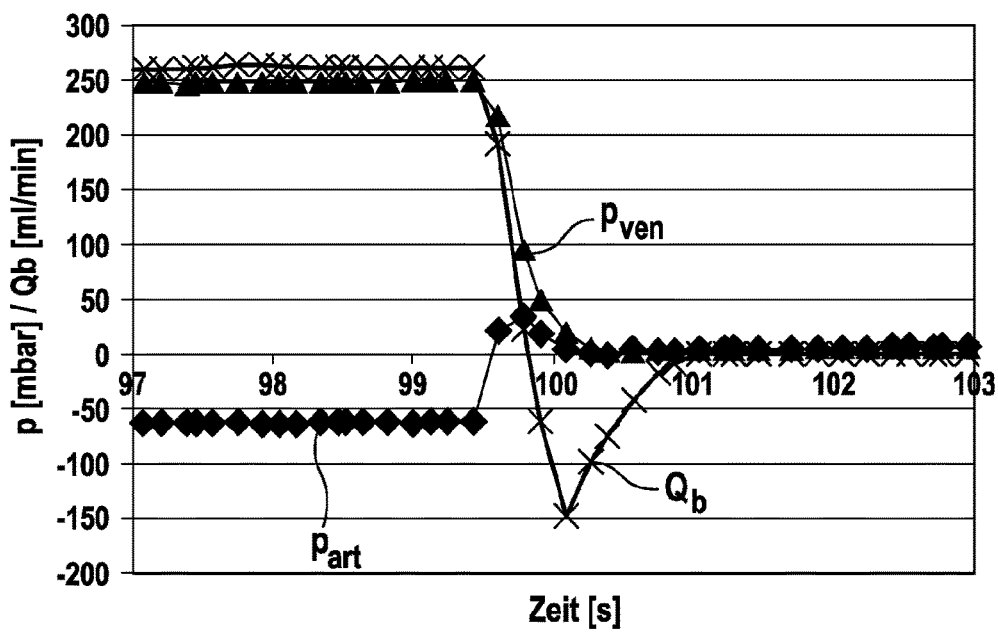
FIG. 3 shows the pressures and the through-flow in the extracorporeal blood circuit when the non-occluding pump is shut off and the shut-off elements are closed at the same time.

Control of the blood treatment apparatus provides for a control mode for shutting off the blood pump 6 or for reducing its speed of rotation. In experiments, it has been shown that if the first and the second shut-off element 9, 10 are closed and the blood pump 6 is shut off, all at the same time, blood flows through the arterial blood feed line 5 back to the patient, although the arterial shut-off element 9 is closed when the blood pump 6 is shut off. FIG. 3 shows the pressure conditions in the extracorporeal blood circuit when the first and the second shut-off element 9, 10 are closed and the blood pump 6 is stopped, all at the same time. In FIG. 3, the arterial pressure measured using the first sensor 21A upstream from the blood pump 6 is referred to as $p_{art}$, the pressure measured using the second sensor 21B is referred to as $p_{pre}$, and the venous pressure measured using the third sensor 21C is referred to as $p_{ven}$. The blood flow measured using the sensor 23A upstream from the blood pump 6 in the blood feed line 5 is indicated in FIG. 3 with $Q_b$.

It has been shown in experiments that the first and the second shut-off element 9, 10 need a certain period of time to clamp off the tube lines, and for this reason the pressure in the lines does not decrease suddenly. While the tube clamps are closing, a reverse flow of blood occurs in the blood feed line 5, in the direction of the patient. In the measurement, the reverse flow rate amounted to as much as approximately 150 ml/min, which corresponds to approximately half the flow rate in the other direction to the dialyzer 1.

In the following, it will be described in detail how the central control unit 20 of the blood treatment apparatus according to the invention controls the individual components of the blood treatment apparatus in control mode, to stop or reduce the speed of rotation of the blood pump 6, in order to prevent an uncontrolled reverse flow to the patient.

First, the control unit 20 closes the first and the second shut-off element 9, 10 at the same time, at a point in time $t_1$. Only after a predetermined time interval $\Delta t$, at a point in time $t_2$, does the control unit 20 stop the blood pump 6 or reduce its speed of rotation. Delayed stopping of the blood pump 6 or reduction of the speed of rotation has the result that an excess pressure builds up in the extracorporeal blood circuit I, so that a reverse flow to the patient cannot take place. In the present exemplary embodiment, the time interval $\Delta t$ is a fixed, predetermined time interval. The time delay for stopping the pump 6 can be a value stored in a memory of the control unit, for example.

Figure 4:
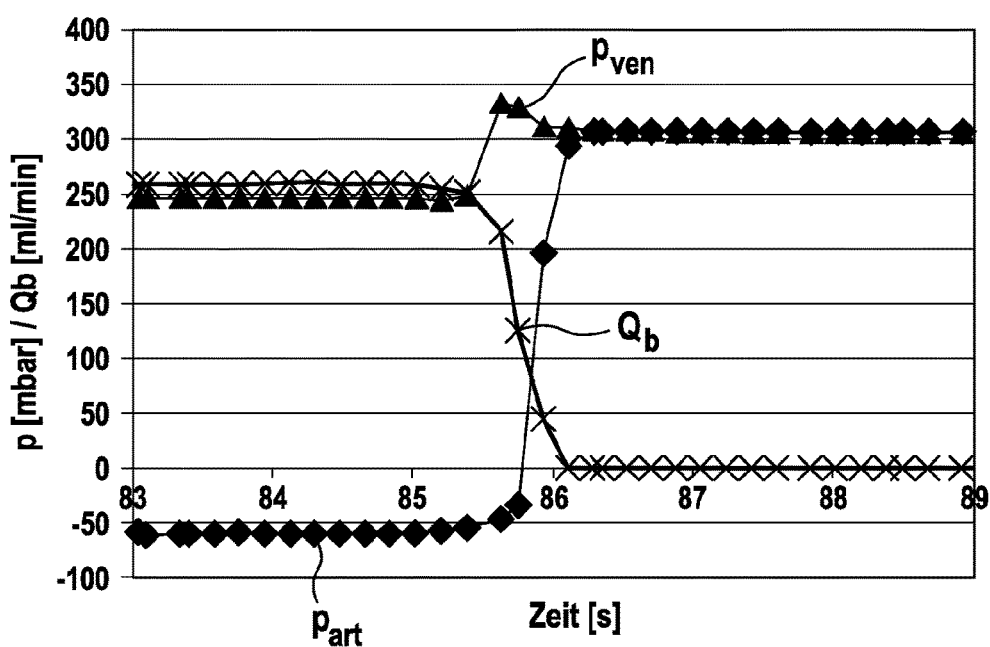
FIG. 4 shows the pressures and the through-flow in the extracorporeal blood circuit when the non-occluding pump is shut off and the shut-off elements are closed according to the method according to the invention.

FIG. 4 shows the pressure and flow conditions when stopping the blood pump 6 and closing the shut-off elements 9, 10 according to the method according to the invention. The build-up of excess pressure in the extracorporeal blood circuit I is shown. The arterial blood flow $Q_b$ drops from approximately 250 ml/min to zero, while the pressure $p_{art}$, $p_{pre}$, $p_{ven}$ in the blood circuit I increases to approximately 300 mbar. A drop in the blood flow to zero occurs, without any reverse flow. In the exemplary embodiment shown in FIG. 4, the blood pump 6 was stopped approximately 1.2 seconds after the shut-off elements 9, 10 were closed.

An embodiment of the invention provides for stopping of the blood pump 6 not after a fixed, predetermined time interval $\Delta t$, but rather at a point in time $t_3$ when the blood flow $Q_b$ approaches the zero point or becomes zero. In this embodiment, the control unit 20 receives the measurement signal measured by the through-flow measurement device 23, where the control unit compares the measured blood flow $Q_b$ with a predetermined limit value that is greater than zero by a specific, preferably slight value, or equal to zero. If the through-flow $Q_b$ at the time point $t_3$ is equal to the limit value, the control unit 20 stops the blood pump 6 or reduces its speed of rotation.

If an uncontrolled blood flow is to be prevented also when turning the blood pump 6 on again or increasing the speed of rotation, a reduction in the excess pressure in the blood circuit I is required. To reduce the excess pressure, a device 24 is provided, which can comprise different components that are already present in a blood treatment apparatus in any case.

In one embodiment, the control unit 20 puts the ultrafiltration pump 19 of the ultrafiltration device 17 into operation for a predetermined time interval, in order to reduce the pressure before opening the first and the second shut-off element 9, 10, so that the excess pressure is reduced by way of the semi-permeable membrane 2 of the dialyzer 1 (FIG. 1). Another embodiment provides a ventilation valve 25 provided on the air separator 8 for reducing the excess pressure before the shut-off elements 9, 10 are opened, which valve is connected with the control unit 20 by way of a control line 25'. The control unit 20 first opens the ventilation valve 25 for a predetermined time interval Δt, and only then opens the first and the second shut-off element 9, 10.

In the alternative embodiment of FIG. 2, the control unit 20 sets different conveying rates for the dialysis fluid pump 16 disposed in the dialysis fluid discharge line 13 and the dialysis fluid pump 26 disposed in the dialysis fluid feed line 11, in order to reduce the excess pressure, where the dialysis fluid pump 16 disposed in the dialysis fluid discharge line is operated at a greater conveying rate (speed of rotation) than the dialysis fluid pump 26 disposed in the dialysis feed line 11, so that fluid (ultrafiltrate) is extracted from the fluid system.

In a further embodiment, the control unit 20 puts the blood pump 6 into operation for a predetermined time interval Δt in order to reduce the excess pressure before opening the first and the second shut-off element 9, 10. Preferably, the blood pump 6 is operated at a predetermined speed of rotation n until a predetermined partial vacuum $p_{art}$ occurs in the arterial blood feed line 5 upstream from the pump. The partial vacuum is monitored using the sensor 21B of the pressure measurement device 21, where the control unit 20 receives the pressure signals measured by the pressure measurement device, and opens the first and the second shut-off element after the required partial vacuum has been reached. The build-up of the partial vacuum in the blood circuit I can also be advantageously combined with the other methods, as an additional measure.

A further embodiment provides that the control unit 20 first opens the second shut-off element 10 in the venous blood discharge line 7 at a first time point $t_1$, and only opens the first shut-off element in the arterial blood feed line 5 at a time point $t_2$ that follows the predetermined time point Δt. As a result, blood can flow into the patient only by way of the venous line 5, but not back to the patient by way of the arterial line 7.

The invention claimed is:

1. An extracorporeal blood treatment apparatus comprising:
   a fluid system comprising a blood feed line that leads to a blood treatment unit, and a blood discharge line that leads away from the blood treatment unit, wherein the blood treatment unit is divided into a blood chamber and a dialysis fluid chamber by means of a semi-permeable membrane,
   a pump configured to (1) convey blood in the blood feed line or in the blood discharge line of the fluid system, or (2) convey dialysis fluid through the dialysis fluid chamber, wherein the pump is a non-occluding pump,
   a first shut-off element for shutting off the blood feed line and a second shut-off element for shutting off the blood discharge line, and
   a control unit for controlling the first shut-off element, the second shut-off element and the non-occluding pump, wherein the control unit is configured such that before the speed of rotation of the pump is reduced or before the pump is shut off, the first shut-off element and the second shut-off element are closed, and the speed of rotation of the pump is reduced or the pump is shut off only after a predetermined time interval has lapsed, the predetermined time interval beginning after the first shut-off element and the second shut-off element are closed.

2. The extracorporeal blood treatment apparatus according to claim 1, wherein the fluid system is an extracorporeal blood circuit of the blood treatment apparatus, the blood feed line is connected with an inlet of the blood chamber, the blood discharge line is connected with an outlet of the blood chamber, and the pump is disposed in the blood feed line.

3. The extracorporeal blood treatment apparatus according to claim 1, further comprising a measuring device for measuring a flow through the blood feed line, wherein the control unit is configured such that the speed of rotation of the pump is reduced at a point in time or the pump is shut off at a point in time when the through-flow measured in the blood feed line is less than or equal to a predetermined limit value.

4. The extracorporeal blood treatment apparatus according to claim 1, further comprising a device for reducing an excess pressure in the fluid system, wherein the control unit is configured such that, after the speed of rotation of the pump is reduced, or after the pump is shut off, the device for reducing an excess pressure is activated before the first shut-off element and the second shut-off element are opened, such that the excess pressure in the fluid system is reduced.

5. The extracorporeal blood treatment apparatus according to claim 4, wherein the device for reducing an excess pressure comprises a ventilation valve configured to be activated by the control unit.

6. The extracorporeal blood treatment apparatus according to claim 5, further comprising an air separator disposed in the blood discharge line, wherein the ventilation valve is provided on the air separator.

7. The extracorporeal blood treatment apparatus according to claim 4, further comprising:
   an ultrafiltration device comprising an ultrafiltration pump configured to be activated by the control unit, wherein the device for reducing an excess pressure comprises the ultrafiltration pump of the ultrafiltration device; or
   an ultrafiltration device comprising a first dialysis fluid pump disposed in a dialysis fluid discharge line and a second dialysis fluid pump disposed in a dialysis fluid feed line, wherein the first dialysis fluid pump and the second dialysis fluid pump are configured to be activated by the control unit, and wherein the device for reducing an excess pressure comprises the first dialysis fluid pump and the second dialysis fluid pump.

8. The extracorporeal blood treatment apparatus according to claim 1, wherein the control unit is configured such that, after the speed of rotation of the pump is reduced or the pump is shut off, and before the pump is turned on or the speed of rotation of the pump is increased, the second shut-off element is opened at a first point in time, and the first shut-off element is opened at a subsequent, second point in time.

9. The extracorporeal blood treatment apparatus according to claim 1, wherein the control unit is configured such that, after the speed of rotation of the pump is reduced or the pump is shut off, the pump is turned on before the first shut-off element and the second shut-off element are opened, or the speed of rotation of the pump is increased before the first shut-off element and the second shut-off element are opened.

10. The extracorporeal blood treatment apparatus according to claim 9, wherein the control unit is configured such that the pump is operated at a speed of rotation while the first shut-off element is closed so that a predetermined partial vacuum builds up in the blood feed line.

11. A method for shutting off or reducing the speed of rotation of a non-occluding pump in a fluid system of an extracorporeal blood treatment apparatus, wherein the fluid system comprises a blood feed line that leads to a blood treatment unit, and a blood discharge line that leads away from the blood treatment unit, and wherein the blood treatment unit is divided into a blood chamber and a dialysis fluid chamber by means of a semi-permeable membrane, the method comprising:
  conveying, with the non-occluding pump, (1) blood through the blood feed line and the blood chamber, or (2) dialysis fluid through the dialysis fluid chamber;
  before the speed of rotation of the non-occluding pump is reduced or before the non-occluding pump is shut off, interrupting a fluid flow into the blood feed line and out of the blood discharge line; and
  after a predetermined time interval has elapsed following the interruption of the fluid flow into the blood feed line and out of the blood discharge line, reducing the speed of rotation of the non-occluding pump or shutting off the non-occluding pump.

12. The method according to claim 11, wherein the fluid system is an extracorporeal blood circuit of the blood treatment apparatus, wherein the blood feed line is connected with an inlet of the blood chamber, the blood discharge line is connected with an outlet of the blood chamber, and the non-occluding pump is disposed in the blood feed line.

13. The method according to claim 11, wherein the speed of rotation of the non-occluding pump is reduced at a point in time, or the non-occluding pump is shut off at a point in time when the through-flow measured in the blood feed line is less than or equal to a predetermined limit value.

14. The method according to claim 13, wherein the predetermined limit value is zero.

15. The method according to claim 11, wherein the extracorporeal blood treatment apparatus comprises a first shut-off element for shutting off the blood feed line and a second shut-off element for shutting off the blood discharge line, the method further comprising:
  after the speed of rotation of the non-occluding pump is reduced, or after the non-occluding pump is shut off, reducing an excess pressure in the fluid system before the first shut-off element and the second shut-off element are opened.

16. The method according to claim 15, wherein reducing the excess pressure is done by activating a ventilation valve provided in the extracorporeal blood treatment apparatus.

17. The method according to claim 15, wherein the extracorporeal blood treatment apparatus further comprises:
  an ultrafiltration device comprising an ultrafiltration pump configured to be activated by a control unit, wherein reducing the excess pressure is done by activating the ultrafiltration pump of the ultrafiltration device; or
  an ultrafiltration device comprising a first dialysis fluid pump disposed in a dialysis fluid discharge line and a second dialysis fluid pump disposed in a dialysis fluid feed line, wherein reducing the excess pressure is done by operating the first dialysis fluid pump and the second dialysis fluid pump at different conveying rates.

18. The method according to claim 11, further comprising:
  after the speed of rotation of the non-occluding pump is reduced, or after the non-occluding pump is shut off, cancelling out interruption of the fluid flow out of the blood discharge line at a first point in time, and cancelling out interruption of the fluid flow into the blood feed line at a subsequent, second point in time, before the non-occluding pump is turned on or before the speed of rotation of the non-occluding pump is increased.

19. The method according to claim 18, wherein, after the speed of rotation of the non-occluding pump is reduced or after the non-occluding pump is shut off, the non-occluding pump is turned on before the interruption of the fluid flow into the blood feed line and the interruption of the fluid flow out of the blood discharge line are cancelled out.

20. The method according to claim 19, wherein the non-occluding pump is operated at a predetermined speed of rotation such that a predetermined partial vacuum occurs in the blood feed line.

21. The extracorporeal blood treatment apparatus according to claim 1, wherein the blood feed line leads to the blood chamber, and the blood discharge line leads away from the blood chamber.

22. The method according to claim 11, wherein the fluid flow is a blood flow, the blood feed line leads to the blood chamber, and the blood discharge line leads away from the blood chamber.

* * * * *